United States Patent [19]
Yuasa et al.

[11] Patent Number: 5,969,131
[45] Date of Patent: Oct. 19, 1999

[54] CEPHEM COMPOUND, ITS PRODUCTION AND ITS USE FOR PRODUCING CEPHEM ANTIBIOTICS

[75] Inventors: Mari Yuasa; Kazuyuki Yamagata, both of Toyonaka; Hirokazu Murata; Masashi Komatsu, both of Ibaraki; Isao Yoshida, Ikeda, all of Japan

[73] Assignee: Sumitomo Chemical Company, Limited, Osaka, Japan

[21] Appl. No.: 08/932,835

[22] Filed: Sep. 18, 1997

Related U.S. Application Data

[62] Division of application No. 08/273,912, Jul. 12, 1994, Pat. No. 5,708,165.

[30] Foreign Application Priority Data

| Jul. 14, 1993 | [JP] | Japan | 5-174441 |
| Nov. 2, 1993 | [JP] | Japan | 5-274183 |
| Jun. 8, 1994 | [JP] | Japan | 6-126303 |

[51] Int. Cl.[6] .............. C07D 501/20; C07D 501/04
[52] U.S. Cl. ............................. 540/215; 540/222
[58] Field of Search ..................... 540/215, 222

[56] References Cited

U.S. PATENT DOCUMENTS

| 4,486,586 | 12/1984 | Narita | 544/22 |
| 4,751,295 | 6/1988 | Oka | 540/222 |
| 4,874,856 | 10/1989 | Iimura | 540/222 |
| 5,095,012 | 3/1992 | Okita | 540/222 |
| 5,373,000 | 12/1994 | Machida | 540/222 |
| 5,373,001 | 12/1994 | Aszodi | 540/222 |
| 5,401,841 | 3/1995 | Asher | 540/222 |

FOREIGN PATENT DOCUMENTS

| 2085137 | 6/1993 | Canada . |
| 264091 | 4/1988 | European Pat. Off. . |
| 0333154 | 9/1989 | European Pat. Off. . |
| 475150 | 3/1992 | European Pat. Off. . |
| 3620995 A1 | 1/1987 | Germany . |
| 03-57106 | 7/1986 | Japan . |
| 3-57106 | 7/1986 | Japan . |
| 5-294974 | 11/1993 | Japan . |
| 2173798 A | 10/1986 | United Kingdom . |
| 87/03875 | 7/1987 | WIPO . |

OTHER PUBLICATIONS

Schwartz, J. Org. Chem 51, 260, 1986.
Seymour Mark, Stereoisomerism In Pharmaceuticals, The Pharmaceutical Journal, Jan. 6, 1990, pp. 25–29.
M. Schwarz et at., "Insect Sex Pheromones. Stereospecific Synthesis of (E)–13, 13–Dimethyl–11–tetradecen–1–01 Acetate via a Thiophenol–Mediated Olefin Inversion", J. Org. Chem., vol. 51, No. 2, 1986, pp. 260–263.

*Primary Examiner*—Mark L. Berch
*Attorney, Agent, or Firm*—Sughrue, Mion, Zinn, Macpeak & Seas, PLLC

[57] ABSTRACT

A 3-[(E)-1-propenyl]cephem compound represented by formula (I):

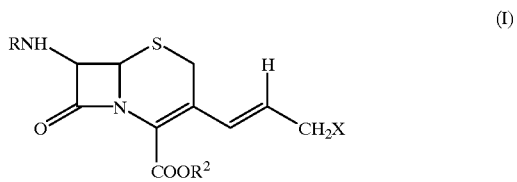

(I)

wherein R represents hydrogen, a protective group for an amino group, or the group shown by formula (II):

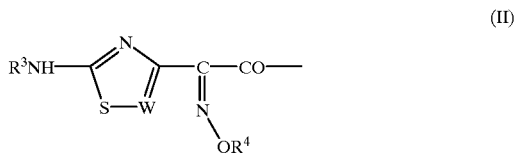

(II)

in which $R^3$ is a protective group for an amino group, $R^4$ is a protective group for a hydroxyl group, and W is —CH= or —N=; $R^2$ represents a protective group for a carboxyl group; and X represents hydrogen or chlorine. The compound is useful as an intermediate for producing cephem antibiotics and is prepared by isomerizing the corresponding 3-[(Z)-1-propenyl]cephem compound in an inert organic solvent in the presence of an aromatic thiol. The compound of formula (I) wherein X is chlorine can be converted into a 3-[(E)-3-ammonio-1-propenyl]cephem derivative through the reaction with a tertiary amine.

2 Claims, No Drawings

CEPHEM COMPOUND, ITS PRODUCTION AND ITS USE FOR PRODUCING CEPHEM ANTIBIOTICS

This is a divisional of application Ser. No. 08/273,912 filed Jul. 12, 1994 U.S. Pat. No. 5,708,165.

The present invention relates to cephem compounds which are useful as intermediates for the production of cephem antibiotics, and a process for producing the same, as well as their use for the preparation of cephem antibiotics or precursors thereof.

For the preparation of cephem antibiotics containing (E)-propenyl group at the 3-position thereof, there is known a process described in, e.g., Japanese Patent KOKOKU No. 3-57106 (corresponding to U.S. Pat. No. 4,751,295) which comprises reacting a (Z)-3-[3-chloro-1-propenyl]cephem compound obtained by Wittig reaction with sodium iodide to isomerize the (Z)-3-[3-chloro-1-propenyl]cephem compound and simultaneously cause halogen exchange to give the 3-[(E)-3-iodo-1-propenyl]cephem compound as the intermediate and then reacting the 3-[(E)-3-iodo-1-propenyl]cephem compound with a tertiary amine to give the ammonio-compound. However, the process encounters problems for industrial production that the intermediate 3-[(E)-3-iodo-1-propenyl]cephem compound is not sufficiently stable and the yield of the intermediate is not satisfactorily high. As a matter of course, the yield of the ammonio-cephem derivatives obtained via the intermediate is not always satisfactory.

In order to establish a process producing cephem antibiotics or their precursors which can be replaced for the disadvantageous prior art process using 3-[(E)-3-iodo-1-propenyl]cephem compounds as the intermediate, the present inventors have made extensive investigations. As a result, novel intermediates have been found.

Therefore, an object of the present invention is to provide cephem compounds which are useful as intermediates for the production of cephem antibiotics.

Another object of the present invention is to provide a process for producing such 3-[(E)-1-propenyl]cephem compounds advantageously.

A further object of the present invention is to provide ammonio-cephem derivatives by using specific cephem compounds.

The present invention provides a 3-[(E)-1-propenyl]cephem compound shown by the following formula (Ia):

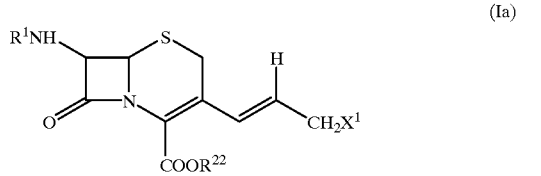

(Ia)

wherein $R^1$ represents hydrogen, a protective group for an amino group, or a group shown by formula (II):

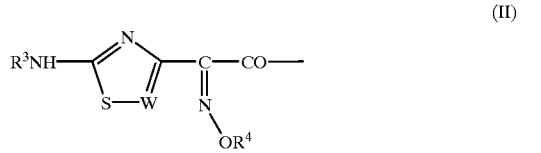

(II)

wherein $R^3$ is a protective group for an amino group, $R^4$ is a protective group for a hydroxyl group and W is CH= or —N=; $R^{22}$ represents a protective group for a carboxyl group; and $X^1$ represents hydrogen or chlorine, provided that $R^1$ is hydrogen when $X^1$ is hydrogen and that $R^{22}$ is not diphenylmethyl when $X^1$ is hydrogen.

The present invention also provides a process for producing a 3-[(E)-1-propenyl]cephem compound represented by formula (I):

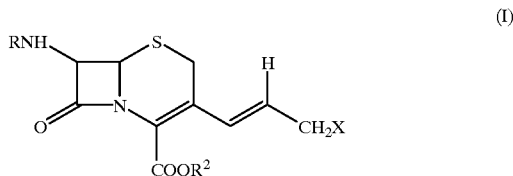

(I)

wherein R represents hydrogen, a protective group for an amino group, or the group shown by formula (II) described above; $R^2$ represents a protective group for a carboxyl group; and X represents hydrogen or chlorine, which comprises isomerizing a 3-[(Z)-1-propenyl]cephem compound represented by formula (III):

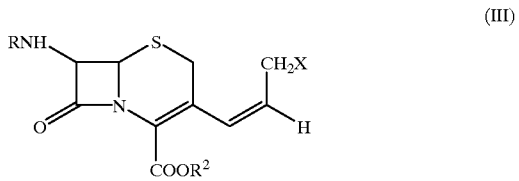

(III)

wherein R, $R^2$ and X are as defined above, in an inert organic solvent in the presence of an aromatic thiol.

The present invention further provides a process for producing a 3-[(E)-3-ammonio-1-propenyl]cephem compound represented by formula (V);

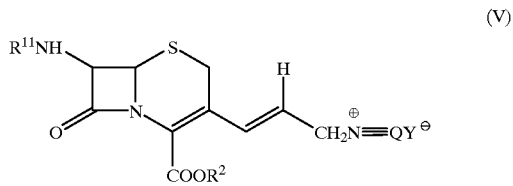

(V)

wherein Rll represents a protecting group for an amino group, or the group shown by formula (II) above; $R^2$ is as defined above; —N≡Q represents an organic quaternary ammonio group; and Y represents a halogen atom; which comprises reacting a compound of formula (Ia) wherein $X^1$ is chlorine, namely, a 3-[(E)-3-chloro-1-propenyl]cephem compound represented by formula (Ib):

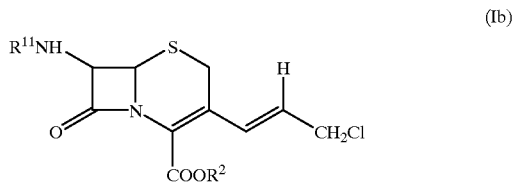

(Ib)

wherein $R^{11}$ and $R^2$ are as defined above, with a tertiary amine in the presence of an iodide or a bromide.

In the process, the 3-[(E)-3-chloro-1-propenyl]cephem compound of formula (Ib) is advantageously prepared by isomerizing the 3-[(Z)-1-propenyl]cephem compound of formula (III) in the presence of the aforesaid aromatic thiol. In this case, the 3-[(Z)-1-propenyl]cephem compound of formula (III) which is a starting compound has chlorine for X and $R^{11}$ of formula (Ib) for R and thus this starting compound is shown by the following formula (IIIb):

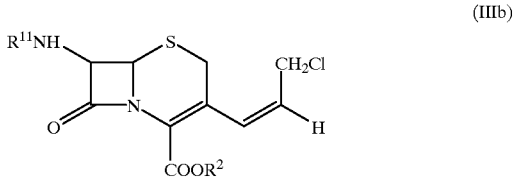

(IIIb)

wherein $R^{11}$ and $R^2$ are as defined above.

In the 3-[(E)-1-propenyl]cephem compound of formula (Ia) of the present invention, the skeletal structure per se is known heretofore. However, the 3-[(E)-1-propenyl]cephem compound of formula (Ia) of the present invention is characterized by its E configuration (trans form) of the propenyl group bound to the cephem skeleton at the 3-position. Accordingly, $R^1$ and $R^{22}$ present on the skeletal structure can cover a variety of groups including known substituents and should be broadly construed.

The compounds represented by formula (I) include the compounds represented by formula (Ia). In formula (I), X is hydrogen or chlorine; R represents hydrogen, a protecting group for an amino group, or the group shown by formula (II) above. In formula (II), $R^3$ represents a protecting group for an amino group, $R^4$ represents a protective group for a hydroxyl group, and W represents —CH= or —N=; the 5-membered heterocyclic ring in formula (II) forms a 1,3-thiazole ring where W represents —CH=, and forms a 1,2,4-thiadiazole ring where W represents —N=.

Where R or $R^1$ represents hydrogen, the amino group shown by RNH— in formula (I) or the amino group shown by $R^1$NE— in formula (Ia) may form a salt with an acid. Examples of acids for forming such salts include mineral acids such as hydrochloric acid, hydrobromic acid, sulfuric acid and phosphoric acid, and organic acids such as acetic acid and trifluoroacetic acid.

The protective group for an amino group which is shown by R in formula (I), $R^1$ in formula (Ia) or $R^3$ in formula (II) means a group that is used to temporarily protect an amino group upon any reaction at other reactive sites in the field of organic synthetic chemistry. These protective groups are specifically an unsubstituted or substituted lower alkanoyl group, an unsubstituted or substituted lower alkoxycarbonyl group, a methyl group mono-, di- or tri-substituted by aromatic rings and a tri-substituted silyl group. The substituent of the substituted lower alkanoyl group may be a halogen, an aromatic ring or a heterocyclic ring. Representative examples of the unsubstituted or substituted lower alkanoyl group include formyl, acetyl, chloroacetyl, dichloroacetyl, phenylacetyl and thienylacetyl. The substituent of the substituted lower alkoxycarbonyl group may be, e.g., an aromatic ring and specific examples of the unsubstituted or substituted lower alkoxycarbonyl group include t-butoxycarbonyl and benzyloxycarbonyl. Specific examples of the methyl group substituted by aromatic rings are p-methoxybenzyl, diphenylmethyl and trityl. A typical example of the tri-substituted silyl group is trimethylsilyl.

Throughout the specification, the term "lower" referred to in a lower alkyl, lower alkoxy, lower alkanoyl group, etc. is used to mean a group having 1 to 6 carbon atoms, preferably 1 to 4 carbon atoms.

The protective group for a hydroxyl group which is shown by $R^4$ in formula (II) means a group that is used to temporarily protect a hydroxyl group upon any reaction at other reactive sites in the field of organic synthetic chemistry. These protective groups are specifically an unsubstituted or substituted lower alkyl group and a tri-substituted silyl group. Representative examples of the unsubstituted lower alkyl group include methyl, ethyl, propyl, isopropyl, butyl, isobutyl, sec-butyl and t-butyl. As the substituent of the substituted lower alkyl groups, there are, for example, a cyano group, a halogen, an aromatic ring and a lower alkanoyloxy group. Specific examples of the cyano-substituted lower alkyl group include cyanomethyl, cyanoethyl and cyanopropyl. The halogen in the halogen-substituted lower alkyl group may be fluorine and chlorine and specific examples of such halogen-substituted lower alkyl group include fluoromethyl, difluoromethyl, 2-fluoroethyl, 2,2-difluoroethyl, 2,2,2-trifluoroethyl, 1-fluoroethyl, 2-fluoropropyl, 1-fluoromethyl-2-fluoroethyl, 3-fluoropropyl and 2,2,2-trichloroethyl. The alkyl group in the aromatic ring-substituted lower alkyl group may be methyl preferably and specific examples of such substituted lower alkyl group include p-methoxybenzyl, p-nitrobenzyl and diphenylmethyl. The lower alkanoyl group in the lower alkanoyloxy-substituted lower alkyl group is preferably a t-alkylcarbonyl group and a representative example of the lower alkanoyloxy-substituted lower alkyl group is pivaloyloxymethyl. Specific examples of the tri-substituted silyl group are the same as those shown for the protecting group for an amino group. Among these groups, a preferred example of $R^4$ is a fluorine-substituted lower alkyl group.

$R^2$ in formula (I) and $R^{22}$ in formula (Ia) represent a protective group for a carboxyl group. The protective group for a carboxyl group referred to herein also means a group that is used to temporarily protect a carboxyl group upon any reaction at other sites in the field of organic synthetic chemistry. These protective groups are specifically an unsubstituted or substituted lower alkyl group and a tri-substituted silyl group. Representative examples of the unsubstituted lower alkyl group are methyl and t-butyl. As the substituent of the substituted lower alkyl group, there are, for example, a halogen, an aromatic ring and a lower alkanoyloxy group. Specific examples of the halogen-substituted lower alkyl group are the same as those of the protecting group for a hydroxyl group indicated hereinabove and 2,2,2-trichloroethyl is particularly preferable. Specific examples of the aromatic ring-substituted lower alkyl group and the lower alkanoyloxy-substituted lower alkyl group are also the same as those of the protective group for a hydroxyl group also indicated hereinabove, provided that $R^{22}$ is not diphenylmethyl where $X^1$ in formula (Ia) is hydrogen. Specific examples of the tri-substituted silyl group are the same as those exemplified for the protecting group for an amino group hereinabove. Preferred examples of $R^2$ and $R^{22}$ where X or $X^1$ is chlorine include p-methoxybenzyl and diphenylmethyl. As a preferred example of $R^{22}$ where $X^1$ is hydrogen, there is p-methoxybenzyl.

The protective group shown by R (or $R^1$), $R^2$ (or $R^{22}$), $R^3$ and $R^4$ may also be introduced into the precursors of the compounds shown by formula (III), using a silylating agent such as N,O-bis(trimethylsilyl)acetamide, N-methyl-N-(trimethylsilyl)acetamide, N-methyl-N-(trimethylsilyl)fluoroacetamide, N-(trimethylsilyl)trimethylsilylacetamide, etc. By the use of these silylating agents, amino and carboxyl groups can be protected at the same time; and where R in formula (I) is the group of formula (II), the amino group corresponding to $R^3$NH— and the hydroxyl group corresponding to —$OR^4$ can be protected simultaneously.

The 3-[(E)-1-propenyl]cephem compounds of formula (Ia) can be prepared by isomerizing the 3-[(Z)-1-propenyl]

cephem compounds of formula (III) in an inert solvent in the presence of an aromatic thiol. The process can also apply not only to the compound of formula (Ia) but also to compounds over a wide range including the case where $R^1$ is not hydrogen or $R^{22}$ is diphenylmethyl when $X^1$ is hydrogen. Accordingly, the 3-[(E)-1-propenyl]cephem compounds prepared by the process can be represented by formula (I) above.

The propenyl group in the starting 3-[(Z)-1-propenyl] cephem compounds of formula (III) is introduced into the cephem skeleton through Wittig reaction as described in, e.g., Japanese Patent KOKAI No. 1-308287 (corresponding to EP-A-333,154). By the Witting reaction, the compounds of formula (III) are obtained generally in the Z form or as a Z form-rich mixture with E form. In the present invention, the compounds of formula (III) can be provided for the isomerization as they stand.

The aromatic thiol used for the isomerization may be unsubstituted or substituted in the aromatic ring by a lower alkyl group such as methyl, ethyl, propyl, isopropyl, butyl, isobutyl, sec-butyl, t-butyl, pentyl or hexyl, a halogen such as fluorine, chlorine, bromine or iodine, a lower alkoxy group such as methoxy, ethoxy or propoxy. Specific examples of the aromatic thiol include thiophenol, 4-chlorothiophenol, 3,4-dichlorothiophenol and 4-t-butylthiophenol. These aromatic thiols may be used alone in combination of two or more thereof. An amount of the aromatic thiol used is generally in the range of 0.05 to 5 moles, preferably 0.1 to 1 mole, more preferably 0.2 to 1 mole, based on 1 mole of the 3-[(Z)-1-propenyl]cephem compound of formula (III).

In the isomerization, a radical initiator may also be used in combination with the aromatic thiol. Examples of the radical initiator which can be used in combination with the aromatic thiol in the present invention are azo compounds such as 2,2'-azobisiso-butyronitrile, 2,2'-azobis(2,4-dimethyl-valeronitrile), etc.; and peroxides such as t-butyl hydroperoxide, benzoyl peroxide, etc. Where the radical initiator is employed, an amount of the radical initiator used is generally in the range of 0.05 to 5 moles, preferably 0.05 to 2 moles, more preferably 0.05 to 0.5 mole, based on 1 mole of the 3-[(Z)-1-propenyl]cephem compound of formula (III).

The reaction is carried out in an inert organic solvent. As the solvent suitable for use, there are, for example, aromatic hydrocarbon solvents, halogenated aliphatic hydrocarbon solvents, lower alkylnitrile solvents and ether solvents. Specific examples of the aromatic hydrocarbon solvents are benzene, toluene, xylene and chlorobenzene; specific examples of the halogenated aliphatic hydrocarbon solvents are methylene chloride, chloroform, 1,1-dichloroethane, 1,2-dichloroethane, 1,1,2-trichloroethane, 1,1,2,2-tetrachloroethane, trichloroethylene and perchloroethylene; specific examples of the lower alkylnitrile solvents are acetonitrile and propionitrile; and specific examples of the ether solvents are diethyl ether and tetrahydro-furan. These solvents may be used alone or in combination of two or more thereof. Inter alia, a solvent mixture of the halogenated aliphatic hydrocarbon and the aromatic hydrocarbon is preferably used. An amount of the solvent used may vary depending upon the kind of solvent but is generally in the range of 1 to 15 parts by weight, preferably 5 to 10 parts by weight, per part by weight of 3-[(Z)-1-propenyl]cephem compound of formula (III).

The isomerization is carried out preferably at a temperature of 10 to 120° C., more preferably 25 to 110° C. At a temperature lower than 10° C., the reaction becomes slow; at a higher temperature above 120° C., the product deteriorates so that the yield might decrease sometimes. Accordingly, the reaction temperature is preferably chosen from the range described above.

After the reaction is completed, the desired product can be obtained, where the reaction is carried out at a temperature higher than room temperature, by cooling the reaction mixture to room temperature and isolating the precipitates from the mother liquor through filtration or the like. Where the reaction is carried out around room temperature, the precipitates are isolated to obtain the desired product. The product is ready for the subsequent reaction, but may also be purified, if necessary, by recrystallization or column chromatography.

In these reactions, some of the Z form may remain in the product, but the 3-[(E)-1-propenyl]cephem compound of formula (I) or formula (Ia) amounts to at least 75 wt %. By appropriately selecting the reaction conditions, the compound of formula (I) or formula (Ia) can be obtained in a purity of not less than 90 wt %, or even in a purity of not less than 95 wt %.

Specific 3-[(E)-1-propenyl]cephem compounds of formula (Ia) thus prepared are listed below.

p-Methoxybenzyl 7β-[2-phenylacetamido]-3-[(E)-3-chloro-1-propenyl]-3-cephem-4-carboxylate Diphenylmethyl 7β-[2-phenylacetamido]-3-[(E)-3-chloro-1-propenyl]-3-cephem-4-carboxylate p-Methoxybenzyl 7β-benzyloxycarbonylamino-3-[(E)-3-chloro-1-propenyl]-3-cephem-4-carboxylate p-Methoxybenzyl 7β-t-butoxycarbonylamino-3-[(E)-3-chloro-1-propenyl]-3-cephem-4-carboxylate Diphenylmethyl 7β-acetamido-3-[(E)-3-chloro-1-propenyl]-3-cephem-4-carboxylate p-Methoxybenzyl 7β-formamido-3-[(E)-3-chloro-1-propenyl]-3-cephem-4-carboxylate Diphenylmethyl 7β-[2-chloroacetamido]-3-[(E)-3-chloro-1-propenyl]-3-cephem-4-carboxylate p-Nitrobenzyl 7β-[2,2-dichloroacetamido]-3-[(E)-3-chloro-1-propenyl]-3-cephem-4-carboxylate t-Butyl 7β-[2-thienylacetamido]-3-[(E)-3-chloro-1-propenyl]-3-cephem-4-carboxylate Methyl 7β-tritylamino-3-[(E)-3-chloro-1-propenyl]-3-cephem-4-carboxylate 2,2,2-Trichloroethyl 7β-[2-phenylacetamido]-3-[(E)-3-chloro-1-propenyl]-3-cephem-4-carboxylate Pivaloyloxymethyl 7β-[2-phenylacetamido]-3-[(E)-3-chloro-1-propenyl]-3-cephem-4-carboxylate Trimethylsilyl 7β-trimethylsilylamino-3-[(E)-3-chloro-1-propenyl]-3-cephem-4-carboxylate p-Methoxybenzyl 7β-amino-3-[(E)-1-propenyl]-3-cephem-4-carboxylate p-Methoxybenzyl 7β-[2-(2-t-butoxycarbonylamino-1,3-thiazol-4-yl)-(Z)-2-(fluoromethoxyimino)acetamido]-3-[(E)-3-chloro-1-propenyl]-3-cephem-4-carboxylate Diphenylmethyl 7β-[2-(2-tritylamino-1,3-thiazol-4-yl)-(Z)-2-(difluoromethoxyimino)acetamido]-3-[(E)-3-chloro-1-propenyl]-3-cephem-4-carboxylate p-Methoxybenzyl 7β-[2-(2-acetamido-1,3-thiazol-4-yl)-(Z)-2-(fluoromethoxyimino)acetamido]-3-[(E)-3-chloro-1-propenyl]-3-cephem-4-carboxylate Diphenylmethyl 7β-[2-(2-formamido-1,3-thiazol-4-yl)-(Z)-2-(difluoromethoxyimino)acetamido]-3-[(E)-3-chloro-1-propenyl]-3-cephem-4-carboxylate p-Methoxybenzyl 7β-[2-(2-t-butoxycarbonylamino-1,3-thiazol-4-yl)-(Z)-2-(2-fluoroethoxyimino)acetamido]-3-[(E)-3-chloro-1-propenyl]-3-cephem-4-carboxylate Diphenylmethyl 7β-[2-(2-tritylamino-1,3-thiazol-4-yl)-(Z)-2-(2,2-difluoroethoxyimino)acetamido]-3-[(E)-3-chloro-1-propenyl]-3-cephem-4-carboxylate p-Methoxybenzyl 7β-[2-(2-acetamido-1,3-thiazol-4-yl)-(Z)-2-(2-fluoropropyloxyimino)acetamido]-3-[(E)-3-chloro-1-propenyl]-3-cephem-4-carboxylate Pivaloyloxymethyl 7β-[2-(2-formamido-1,3-thiazol-4-yl)-(Z)-2-(1-fluoromethyl-2-fluoroethoxyimino)acetamido]-3-[(E)-3-chloro-1-propenyl]-3-cephem-4-carboxylate p-Methoxybenzyl 7β-[2-(2-acetamido-1,3-thiazol-4-yl)-(Z)-2-(3-fluoropropyloxyimino)acetamido]-3-[(E)-3-chloro-1-propenyl]-3-cephem-4-carboxylate p-Nitrobenzyl 7β-[2-(2-formamido-1,3-thiazol-4-yl)-(Z)-2-(1-fluoroethoxyimino)acetamido]-3-[(E)-3-chloro-1-propenyl]-3-cephem-4-carboxylate t-Butyl 7β-[2-(2-formamido-1,3-thiazol-4-yl)-(Z)-2-(2,2,2-trifluoroethoxyimino)acetamido]-3-[(E)-3-chloro-1-propenyl]-3-cephem-4-carboxylate p-Methoxybenzyl 7β-[2-(5-acetamido-1,2,4-thiazol-3-yl)-(Z)-2-(2-cyanoethyloxyimino)acetamido]-3-[(E)-3-chloro-1-propenyl]-3-cephem-4-carboxylate p-Methoxybenzyl 7β-[2-(5-acetamido-1,2,4-thiadiazol-3-yl)-(Z)-2-(3-fluoropropyloxyimino)acetamido]-3-[(E)-3-chloro-1-propenyl]-3-cephem-4-carboxylate As stated hereinabove, not only the compounds of formula (Ia) but also other compounds of formula (I) can be prepared by the isomerization. Compounds other than those listed above may also be prepared by the isomerization of the present invention. Specific examples of such 3-[(E)-1-propenyl]cephem compounds of formula (I) include the following compounds.

Diphenylmethyl 7β-amino-3-[(E)-1-propenyl]-3-cephem-4-carboxylate p-Methoxybenzyl 7β-[2-phenylacetamido]-3-[(E)-1-propenyl]-3-cephem-4-carboxylate Among the thus prepared 3-[(E)-1-propenyl]-cephem compounds of formula (I), the compounds wherein X is hydrogen can be converted into cephem antibiotics disclosed in Japanese Patent KOKAI No. 62-491 (corresponding to U.S. Pat. No. 4,708,955) by acylating the amino group shown by RNH— in formula (I) with 2-aminothiazolic acid and then removing the protecting group for a carboxyl group.

The compound of formula (I) wherein X is chlorine, namely, the 3-[(E)-3-chloro-1-propenyl]cephem compound of formula (Ib) above is reacted with a tertiary amine to quaternize and lead to the 3-[(E)-3-ammonio-1-propenyl]cephem derivative of formula (V) described above.

The tertiary amine used in this reaction may be acyclic or cyclic amine or a combination thereof. The group bound to the tertiary nitrogen may contain a hetero atom such as nitrogen, sulfur or oxygen. Such tertiary amine can be specifically shown by the following formula (IV):

$$N\equiv Q \qquad (IV)$$

wherein $\equiv Q$ represents one, two or three groups having three bonds to the nitrogen and each of the bonds may be independent or two or three of the bonds may be combined together to form a ring which may contain a hetero atom selected from the group consisting of nitrogen, sulfur and oxygen.

The acyclic tertiary amine may be, e.g., a compound shown by formula (IVa):

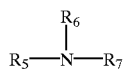

(IVa)

wherein each of $R^5$, $R^6$ and $R^7$ independently represents an unsubstituted or substituted lower alkyl group, an amino group, a ureido group or a hydroxyl group.

Herein examples of the substituent for the substituted lower alkyl group include hydroxyl, carbamoyl, cyano, a lower alkylcarbonylamino, aminosulfonylaminocarbonyl, lower alkylsulfonylaminocarbonyl, lower alkylaminocarbonyl, hydroxy-lower alkylaminocarbonyl, lower alkyloxyaminocarbonyl, hydroxyaminocarbonyl, carbamoyl-lower alkylaminocarbonyl, lower alkylamino, carboxylate-lower alkyl-di-lower alkylammonio, di-lower alkylamino group, carboxyl, a lower alkyloxy, di-lower alkylaminocarbonyl, bis(hydroxy-lower alkyl)aminocarbonyl, bis(hydroxy-lower alkyl)amino group, amino, oxo, and a 5-membered heterocyclic group. The acyclic tertiary amine may be substituted by 1 to 3 substituents selected from the above substituents. As the lower alkyl group substituted by two or three substituents, there are lower alkyl groups substituted by a hydroxyl group and a carbamoyl group, by a hydroxyl group and a hydroxy-lower alkylaminocarbonyl group, by a hydroxyl group and a di-lower alkylamino group, by two carbamoyl groups, by two hydroxyl groups, and by three hydroxyl groups. The 5-membered heterocyclic substituent for the substituted lower alkyl group may be the minimum hydrogenated compound and examples include pyrazolyl, imidazolyl, oxadiazolyl and tetrazolyl.

Examples of the cyclic tertiary amine include the following compounds.

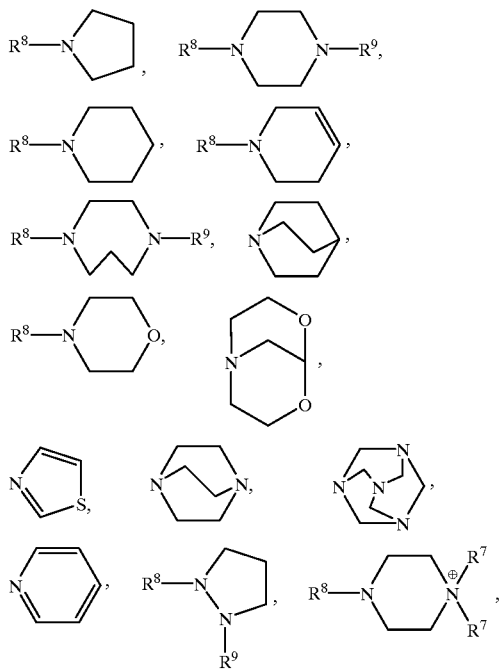

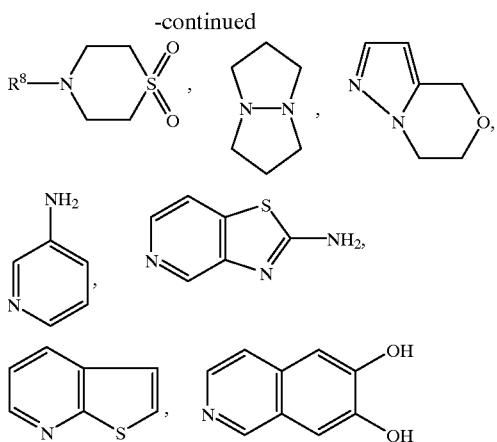

wherein R$^7$ is the same as defined above; R$^8$ represents an unsubstituted or substituted lower alkyl group; and R$^9$ represents a protective group for an amino group.

Furthermore, the cyclic tertiary amines which have substituents on the ring are also used. In the above formula denoting the cyclic tertiary amine, examples of the substituent shown by R$^8$ which may bound to the lower alkyl group are hydroxyl, carbamoyl, cyano, carboxyl and ureido. The lower alkyl group may be substituted by one or two substituents selected from the substituents described above. As the lower alkyl group substituted by two substituents, there is a compound substituted, e.g., by two hydroxyl groups. Specific examples of the protecting group for an amino group represented by R$^9$ are the same as those explained for R, R$^1$ and R$^3$ above. As the substituent which may be bound to the carbon atom for constituting the ring of the cyclic tertiary amine, there are a lower alkyl group which may be unsubstituted or substituted by hydroxyl, carboxyl, hydroxyimino, imino, carboxy-lower alkyloxy or sulfo groups; hydroxyl; formyl; a sulfonic acid group; carbamoyl, sulfamoyl; carboxyl; a bis(hydroxy-lower alkyl) aminocarbonyl group; a hydroxy-lower alkylaminocarbonyl group; amino; morpholinocarbonyl; a carboxy-lower alkylthio group; etc.

Specific examples of the tertiary amine suitable for reacting with the 3-[(E)-3-chloro-1-propenyl]cephem compound of formula (Ib) include 2 -(dimethylamino)acetamide, 2-(ethylmethylamino)acetamide, 2-(diethylamino) acetamide, 2-(dimethylamino)ethanol, 2-(dimethylamino)-3-hydroxypropionamide, D-2-(dimethylamino)-3-hydroxypropionamide, 2-(dimethylamino)-propionamide, D-2-(dimethylamino)propionamide, 1-aza-4,6-dioxabicyclo[3.3.1]nonane, 1-aza-5-methyl-4,6-dioxabicyclo[3.3.1]nonane, 1-aza-5-ethyl-4,6-dioxabicyclo[3.3.1]nonane, 4-carbamoyl-1-(2-hydroxy-ethyl)-piperidine, tris(2-hydroxyethyl)amine, 4-carbamoylquinuclidine, 1-methyl-3-carbamoylpyrrolidine, 1-methylpyrrolidine, 3-aminopyridine, 6,7-dihydroxyisoquinoline, thieno[2,3-b]pyridine, 2-aminothiazolo-[4,5-c]pyridine, hydroxymethylpyridine, carbamoylpyridine, formylaminopyridine, 1-methyl-morpholine, etc. Among them, 2-(ethylmethylamino)-acetamide is preferred.

It is sufficient for the reaction to use the tertiary amine in an amount of approximately 1 to 2 moles, based on 1 mole of the 3-[(E)-3-chloro-1-propenyl]cephem compound of formula (Ib). The tertiary amine may also be used as a solvent in an excess amount, depending upon kind of the amine.

Reaction solvents other than the amine may also be used. As such solvents, there are, for example, a non-protonic organic polar solvent, a lower alkyl ketone solvent, a lower alkylnitrile solvent, a halogenated alkyl solvent and an ether solvent. Specific examples of the non-protonic organic polar solvent include dimethylformamide, dimethylacetamide, dimethylsulfoxide, nitromethane, etc.; specific examples of the lower alkyl ketone solvent are acetone and ethyl methyl ketone; specific examples of the lower alkylnitrile solvent are acetonitrile and propionitrile; specific examples of the halogenated alkyl solvent are dichloromethane and 1,2-dichloroethane; and specific examples of the ether solvent are tetrahydrofuran and dimethoxyethane. These solvents may be used singly or in combination of two or more thereof. Among them, non-protonic organic polar solvents such as dimethylformamide and dimethylsulfoxide are preferably used.

Conversion into the quaternary ammonium using the tertiary amine can be made in the presence of an iodide or a bromide. As the iodide, there may be used an alkali metal iodide such as sodium iodide or potassium iodide, an organic quaternary ammonium iodide such as tetrabutyl ammonium iodide; as the bromide, there may be used an alkali metal bromide such as sodium bromide or potassium bromide, an organic quaternary ammonium bromide such as tetrabutyl ammonium bromide.

These iodides or bromides are employed generally in an amount of approximately 0.1 to 5 moles, preferably approximately 1 to 2 moles, based on 1 mole of the 3-[(E)-3-chloro-1-propenyl]cephem compound of formula (Ib). Where these iodides or bromides are sparingly soluble in the solvent, the reaction can be effected using crown ether or a phase transfer catalyst. The iodide or bromide may also be used less than the equimolar amount to the 3-[(E)-3-chloro-1-propenyl]-cephem compound of formula (Ib); in this case, the compound of formula (V) may be a mixture of the compound herein Y is chlorine and the compound wherein Y is iodine or bromine. The compound of formula (V) wherein Y is chlorine may also be obtained depending upon conditions or post-treatment. Accordingly, the halogen shown by Y in formula (V) may generally be chlorine, bromine or iodine.

The ammonium quaternization is generally conducted at a temperature of 10 to 40° C., preferably 20 to 30° C. When the reaction temperature is lower than 10° C., the reaction proceeds only with difficulty. Where the temperature is higher than 40° C., deterioration of the product tends to occur. It is thus preferred to conduct the quaternization at the reaction temperature within the range given above.

After the reaction is completed, the product can be isolated by means of crystallization, by distillation of the solvent, by a method which comprises adding a poor solvent to the system to solidify the product and withdrawing the product in a non-crystalline state, or by a method of isolating the product with a solvent such as dimethylformamide as solvated crystals.

According to the above procedures, the 3-[(E)-3-ammonio-1-propenyl]cephem derivative wherein Y in formula (V) is iodine or chlorine can be obtained where the reaction is carried out using the iodide and where the reaction is carried out using the bromide, the 3-[(E)-3-ammonio-1-propenyl]cephem derivative wherein Y in formula (V) is bromine or chlorine can be obtained. Examples of ammonium cations in formula (V) include the following.

p-Methoxybenzyl 7β-[2-phenylacetamido]-3-[(E)-3-(carbamoylmethylethylmethylammonio)-1-propenyl]3-3-cephem-4-carboxylate Diphenylmethyl 7β-[2-phenylacetamidol-3-[(E)-3-(carbamoylmethyldimethylammonio)-1-propenyl]-3-cephem-4-carboxylate p-Methoxybenzyl 7β-benzyloxycarbonylamino-3-[(E)-3-(carbamoylmethyldimethylammonio)-1-propenyl]-3-cephem-4-carboxylate p-Methoxybenzyl 7β-t-butoxycarbonylamino-3-((E)-3-(carbamoylmethyldimethylammonio)-1-propenyl]-3-cephem-4-carboxylate Diphenylmethyl 7β-acetamido-3-[(E)-3-{dimethyl(D-1-carboxyethyl)ammonio}-1-propenyl]-3-cephem-4-carboxylate p-Methoxybenzyl 7β-formamido-3-[(E)-3-{tris(2-hydroxyethyl)ammonio}-1-propenyl]-3-cephem-4-carboxylate Diphenylmethyl 7β-[2-chloroacetamido]-3-[(E)-3-{4-carbamoyl-1-(2-hydroxyethyl)piperidinio}-1-propenyl]-3-cephem-4-carboxylate p-Nitrobenzyl 7β-[2,2-dichloroacetamido]-3-[(E)-3-(1-methyl-3-carbamoylpyrrolidinio)-1-propenyl]-3-cephem-4-carboxylate t-Butyl 7β-[2-thienylacetamido]-3-[(E)-3-(4-carbamoylquinuclidinio)-1-propenyl]-3-cephem-4-carboxylate Methyl 7β-tritylamino-3-[1(E)-3-(1-methylpyrrolidinio)-1-propenyl]-3-cephem-4-carboxylate 2,2,2-Trichloroethyl 7β-[2-phenylacetamido]-3-[(E)-3-(3-aminopyridinio)-1-propenyl]-3-cephem-4-carboxylate Pivaloyloxymethyl 7β-[2-phenylacetamido]-3-[(E)-3-(6,7-dihydroxyisoquinolinio)-1-propenyl]-3-cephem-4-carboxylate Trimethylsilyl 7β-trimethylsilylamino-3-[(E)-3-(2-amino-5-thiazolo[4,5-c]pyridinio)-1-propenyl]-3-cephem-4-carboxylate p-Methoxybenzyl 7β-[2-(2-t-butoxycarbonylamino-1,3-thiazol-4-yl)-(Z)-2-(fluoromethoxyimino)acetamido]-3-[(E)-3-(3-hydroxymethylpyridinio)-1-propenyl]-3-cephem-4-carboxylate Diphenylmethyl 7β-[2-(2-tritylamino-1,3-thiazol-4-yl)-(Z)-2-(difluoromethoxyimino)acetamido]-3-[(E)-3-(3-carbamoylpyridinio)-1-propenyl]-3-cephem-4-carboxylate p-Methoxybenzyl 7β-[2-(2-acetamido-1,3-thiazol-4-yl)-(Z)-2-(fluoromethoxyimino)acetamido]-3-[(E)-3-(4-carbamoylpyridinio)-1-propenyl]-3-cephem-4-carboxylate Diphenylmethyl 7β-[2-(2-formamido-1,3-thiazol-4-yl)-(Z)-2-(difluoromethoxyimino)acetamido]-3-[(E)-3-(3-formylaminopyridinio)-1-propenyl]-3-cephem-4-carboxylate p-Methoxybenzyl 7β-[2-(2-t-butoxycarbonylamino-1,3-thiazol-4-yl)-(Z)-2-(2-fluoroethoxyimino)acetamido]-3-[(E)-3-(1-methylmorpholinio)-1-propenyl]-3-cephem-4-carboxylate Diphenylmethyl 7β-[2-(2-tritylamino-1,3-thiazol-4-yl)-(Z)-2-(2,2-difluoroethoxyimino)acetamido]-3-[(E)-3-(1-aza-4,6-dioxabicyclo[3.3.1]nonan-1-io)-1-propenyl]-3-cephem-4-carboxylate p-Methoxybenzyl 7β-[2-(2-acetamido-1,3-thiazol-4-yl)-(Z)-2-(2-fluoropropyloxyimino)acetamido]-3-[(E)-3-(1-aza-5-methyl-4,6-dioxabicyclo[3.3.1]nonan-1-io)-1-propenyl]-3-cephem-4-carboxylate Pivaloyloxymethyl 7β-[2-(2-formamido-1,3-thiazol-4-yl)-(Z)-2-(1-fluoromethyl-2-fluoroethoxyimino)acetamido]-3-[(E)-3-(1-aza-5-ethyl-4,6-dioxabicyclo[3.3.1]nonan-1-io)-1-propenyl]-3-cephem-4-carboxylate p-Methoxybenzyl 7β-[2-(2-acetamido-1,3-thiazol-4-yl)-(Z)-2-(3-fluoropropyloxyimino)acetamido]-3-[(E)-3-(carbamoylmethyldimethylammonio)-1-propenyl]-3-cephem-4-carboxylate p-Methoxybenzyl 7β-[2-(2-acetamido-1,3-thiazol-4-yl)-(Z)-2-(2-cyanoethylimino)acetamido]-3-[(E)-3-(carbamoylmethyldimethylammonio)-1-propenyl]-3-cephem-4-carboxylate p-Nitrobenzyl 7β-[2-(2-formamido-1,3-thiazol-4-yl)-(Z)-2-(1-fluoroethoxyimino)acetamido]-3-[(E)-3-(carbamoylmethyldimethylammonio)-1-propenyl]-3-cephem-4-carboxylate t-Butyl 7β-[2-(2-formamido-1,3-thiazol-4-yl)-(Z)-2-(2,2,2-trifluoroethoxyimino)acetamido]-3-[(E)-3-(7-thieno[2,3-b]pyridinio)-1-propenyl]-3-cephem-4-carboxylate Diphenylmethyl 7β-[2-(5-tritylamino-1,2,4-thiazol-3-yl)-(Z)-2-(difluoromethoxyimino)acetamido]-3-[(E)-3-(3-formylaminopyridinio) 1-propenyl]-3-cephem-4-carboxylate The 3-[(E)-3-ammonio-1-propenyl]cephem derivative of formula (V) may further be subjected to reactions for removing the protective groups and the like, whereby cephem antibiotics can be prepared.

Next the present invention is described below in more detail with reference to the examples below but is not limited thereto. In the examples, % is by weight, unless otherwise indicated.

EXAMPLE 1

In 72 ml of 1,2-dichloroethane were dissolved 10 g (19.5 mmoles) of p-methoxybenzyl 7β-[2-phenylacetamido]-3-[3-chloro-1-propenyl]-3-cephem-4-carboxylate (Z/E=76/24) and 2.0 ml (19.5 mmoles) of thiophenol. The solution was stirred at 60° C. for 2 hours. After completion of the reaction, the reaction mixture was cooled to room temperature. The precipitates formed were collected by filtration to give 7.0 g (13.6 mmoles) of p-methoxybenzyl 7β-[2-phenylacetamido]-3-[3-chloro-1-propenyl]-3-cephem-4-carboxylate (E/Z=95/5). Yield, 70%.

IR absorption spectrum (cm$^{-1}$, KBr transmission method): 3424.3, 1765.5, 1709.2, 1656.1, 1614.3, 960.1

NMR spectrum (δ, DMSO-d$_6$): 3.53 (2H, s), 3.59 (1H, d, J=18.14 Hz), 3.75 (3H, s), 3.90 (1H, d, J=17.81 Hz), 4.31 (2H, d, J=6.93 Hz), 5.15 (1H, d, J=4.95 Hz), 5.22 (2H), 5.71 (1H, dd, J=4.61 Hz, 8.25 Hz), 6.22 (1H, dt, J=15.5 Hz, 6.93 Hz), 6.79 (1H, d, J=15.5 Hz), 6.94 (2H, d, J=8.90 Hz), 7.28 (5H, m), 7.36 (2H, d, J=8.58 Hz), 9.17 (1H, d, J=8.58 Hz)

EXAMPLE 2

In 52 ml of toluene were dissolved 7.5 g (13 mmoles) of diphenylmethyl 7β-[2-phenylacetamido]-3-[3-chloro-1-propenyl]-3-cephem-4-carboxylate (Z/E=99/1) and 0.3 ml (3 mmoles) of thiophenol. After 0.4 g (1.6 mmole) of 2,2'-azobis(2,4-dimethylvaleronitrile) was added to the solution, the mixture was stirred at 60° C. for 2 hours. After completion of the reaction, the reaction mixture was cooled to room temperature. The precipitates formed were collected by filtration to give 6.3 g (11 mmoles) of diphenylmethyl 7β-[2-phenylacetamido]-3-[3-chloro-1-propenyl]-3-cephem-4-carboxylate (E/Z=99/1). Yield, 84%.

IR absorption spectrum (cm$^{-1}$, KBr transmission method): 3431.6, 1779.1, 1712.0, 1653.3, 961.8

NMR spectrum (δ, DMSO-d$_6$): 3.54 (2H, s), 3.62 (1H, d, J=17.8 Hz), 3.92 (1H, d, J=17.8 Hz), 4.17 (2H, d, J=6.9 Hz), 5.19 (1H, s), 5.77 (1H, dd, J=5 Hz, J=8.2 Hz), 6.25 (1H, dt, J=6.9 Hz, J=15.5 Hz), 6.70 (1H, d, J=15.5 Hz), 6.99 (1H, s), 7.51–7.22 (15H, m, br), 9.20 (1H, d, J=8.2 Hz)

EXAMPLE 3

In a solvent mixture of 675 g of dichloromethane and 225 g of toluene were dissolved 100 g (195 mmoles) of p-methoxybenzyl 7β-[2-phenylacetamido]-3-[3-chloro-1-propenyl]-3-cephem-4-carboxylate (Z/E=82/18) and 4.0 ml (39 mmoles) of thiophenol. After 2.4 g (9.8 mmoles) of 2,2'-azobis(2,4-dimethylvaleronitrile) was added to the solution, the mixture was stirred at 60° C. for 2 hours. After completion of the reaction, the reaction mixture was cooled to room temperature. The precipitates formed were collected by filtration to give 81.5 g (159 mmoles) of p-methoxybenzyl 7β-[2-phenylacetamido]-3-[3-chloro-1-propenyl]-3-cephem-4-carboxylate (E/Z=99/1). Yield, 81.5%. The IR absorption spectrum and NMR spectrum of the product coincided with those of the product obtained in Example 1.

EXAMPLES 4–8

Using as a starting compound p-methoxybenzyl 7β-[2-phenylacetamido]-3-[chloro-1-propenyl]-3-cephem-4-carboxylate, isomerization was performed under the conditions shown in Table 1 in a manner similar to Example 3. The results are shown in Table 1.

TABLE 1

| Example No. | 4 | 5 | 6 | 7 | 8 |
|---|---|---|---|---|---|
| Starting material (III) | | | | | |
| E/Z | 18/82 | 18/82 | 21/79 | 21/79 | 21/79 |
| Aromatic thiol | | | | | |
| Kind[1] | B | A | B | C | D |
| Molar ratio[4] | 0.5 | 0.5 | 0.3 | 0.3 | 0.3 |
| Radical initiator | | | | | |
| Kind[2] | AIB | TBHP | AVN | AVN | AVN |
| Molar ratio[4] | 0.15 | 0.15 | 0.16 | 0.16 | 0.16 |
| Solvent | | | | | |
| Kind[3] | b | a | a/c | a/c | a/c |
| Mixing weight ratio | — | — | 2/1 | 2/1 | 2/1 |
| Reaction temperature | 60° C. | 40° C. | 49° C. | 49° C. | 49° C. |
| Reaction time | 2 hrs | 1 hr | 3 hrs | 3 hrs | 3 hrs |
| Product (I) | | | | | |
| Yield | 83% | 70% | 92% | 89% | 84% |
| E/Z | 96.4/3.6 | 98.3/1.7 | 97.3/2.7 | 96.4/3.6 | 93.5/6.5 |

[1]A: thiophenol
B: p-chlorothiophenol
C: 3,4-dichlorothiophenol
D: 4-t-butylthiophenol
[2]AIB: 2,2'-azobisisobutyronitrile
AVN: 2,2'-azobis(2,4-dimethylvaleronitrile)
TBHP: t-butyl hydroperoxide
[3]a: dichloromethane
b: 1,2-dichloroethane
c: toluene
[4]The molar ratio denotes a ratio to the total weight of the starting E/Z mixture.

EXAMPLE 9

In a solvent mixture of 14.23 g of dichloromethane and 4.80 g of toluene were dissolved 1.98 g (4.99 mmoles) of p-methoxybenzyl 7β-amino-3-[1-propenyl]-3-cephem-4-carboxylate hydrochloride (Z/E=90.1/9.9) and 0.53 g (3.66 mmoles) of p-chlorothiophenol. After 0.53 g (2.03 mmoles) of 2,2'-azobis(2,4-dimethyl-valeronitrile) was added to the solution, the mixture was stirred at 60° C. for 9 hours. After completion of the reaction, the reaction mixture was cooled to room temperature. The precipitates formed were collected by filtration to give 1.44 g (3.63 mmoles) of crude p-methoxybenzyl 7β-amino-3-[1-propenyl]-3-cephem-4-carboxylate hydrochloride (E/Z=83.0/17.0). The crude product was recrystallized from methanol/toluene to give 1.18 g (2.98 mmoles) of p-methoxybenzyl 7β-amino-3-[1-propenyl]-3-cephem-4-carboxylate hydrochloride (E/Z=96/4). Yiel: 60%.

IR absorption spectrum (cm$^{-1}$, KBr transmission method): 3438.0, 1775.9, 1713.9, 969.8

NMR spectrum (δ, DMSO-d$_6$): 1.81 (3H, d, J=6.60 Hz), 3.70 (1H, d, J=17.16 Hz), 3.75 (3H, s), 3.90 (1H, d, J=16.82 Hz), 5.12 (2H, d, J=4.95 Hz), 5.19 (1H, s), 5.23 (1H, d, J=4.95 Hz), 6.29 (1H, dq, J=6.76 Hz, J=15.67 Hz), 6.75 (1H, d, J=15.83 Hz), 6.94 (2H, d, J=8.24 Hz), 7.36 (2H, d, J=8.25 Hz), 9.19 (2H, b)

EXAMPLE 10

In a solvent mixture of 14.43 g of dichloromethane and 4.71 g of toluene were dissolved 1.92 g (3.99 mmoles) of p-methoxybenzyl 7β-[2-phenylacetamido]-3-[1-propenyl]-3-cephem-4-carboxylate (Z/E=88.4/11.6) and 0.20 g (1.38 mmoles) of p-chlorothiophenol. After 0.19 g (0.76 mmoles) of 2,2'-azobis(2,4-dimethylvaleronitrile) was added to the solution, the mixture was stirred at 60° C. for 2 hours. After completion of the reaction, the reaction mixture was cooled to room temperature. The precipitates formed were collected by filtration to give 1.54 g (3.20 mmoles) of p-methoxybenzyl 7β-[2-phenylacetamido]-3-[1-propenyl]-3-cephem-4-carboxylate (E/Z=98.0/2.0). Yield: 80.2%.

IR absorption spectrum (cm$^{-1}$, KBr transmission method): 3438.9, 3275.7, 1784.9, 1763.5, 1713.5, 1662.0, 971.1, 698.9

NMR spectrum (δ, DMSO-d$_6$): 1.78 (3H, d, J=6.93 Hz), 3.54 (1H, d, J=17.5 Hz), 3.70 (2H, s), 3.75 (3H, s), 3.86 (1H, d, J=17.5 Hz), 5.11 (1H, d, J=4.95 Hz), 5.19 (2H, s), 5.65 (1H, dd, J=4.62 Hz, J=8.25 Hz), 6.14 (1H, dq, J=6.93 Hz, J=15.8 Hz), 6.56 (1H, d, J=15.8 Hz), 6.94 (2H, d, J=8.90 Hz), 7.28 (5H, m), 7.36 (2H, d, J=8.58 Hz), 9.14 (1H, d, J=8.58 Hz)

EXAMPLE 11

After 10 g (19.5 mmoles) of p-methoxybenzyl 7β-[2-phenylacetamido]-3-[3-chloro-1-propenyl]-3-cephem-4-carboxylate (E/Z=99/1) obtained in Example 3 was suspended in 20 ml of N,N-dimethylformamide, 2.3 g of 2-(ethylmethylamino)-acetamide and 2.9 g (19.3 mmoles) of sodium iodide were added to the suspension. The mixture was stirred at room temperature for 2 hours. To the thus obtained reaction mixture was dropwise added 160 ml of toluene. The formed crystals were filtered to give 14.7 g of p-methoxybenzyl 7β-[2-phenylacetamido]-3-[(E)-3-(carbamoylmethylethylmethylammonio)-1-propenyl]-3-cephem-4-carboxylate iodide N,N-dimethylformamide-solvated salt. Yield: 95%. The overall yield from the previous step (Example 3) was 77%.

EXAMPLE 12

The reaction was carried out under the same conditions as in Example 11 except that 0.5 g (3.3 mmoles) of sodium iodide was used and stirring was conducted for 6 hours. The formed crystals were filtered to give p-methoxybenzyl 7β-[2-phenylacetamido]-3-[(E)-3-(carbamoylmethylethylmethylammonio)-1-propenyl]-3-cephem-4-carboxylate iodide N,N-dimethylformamidesolvated salt and p-methoxybenzyl 7β-[2-phenylacetamido]-3-[(E)-3-(carbamoylmethylethylmethylammonio)-1-propenyl]-3-cephem-4-carboxylate chloride N,N-dimethylformamide-solvated salt. As the result of reversed phase high performance liquid chromatography, the yield of p-methoxybenzyl 7β-[2-phenylacetamido]-3-[(E)-3-(carbamoylmethylethylmethylammonio)-1-propenyl]-3-cephem-4-carboxylate cations was 89.3%.

EXAMPLE 13

After 10 g of p-methoxybenzyl 7β-[2-phenylacetamido]-3-[3-chloro-1-propenyl]-3-cephem-4-carboxylate (E/Z=99/1) was suspended in 50 ml of dichloromethane, 2.3 g of 2-(ethylmethylamino)acetamide and 7.2 g of tetrabutylammonium iodide were added to the suspension. The mixture was stirred at room temperature for 24 hours. The solvent was removed from the reaction mixture by distillation to give an oily substance containing 10.2 g of p-methoxybenzyl 7β-[2-phenylacetamido]-3-[(E)-3-(carbamoylmethylethylmethylammonio)-1-propenyl]-3-cephem-4-carboxylate iodide. Yield; 72%.

EXAMPLE 14

After 1.0 g of diphenylmethyl 7β-[2-phenylacetamido]-3-[3-chloro-1-propenyl]-3-cephem-4-carboxylate (E/Z=99/1) obtained in Example 2 was dissolved in 2.0 g of N,N-dimethylformamide, 0.21 g of 2-(ethylmethylamino)acetamide and 0.28 g of sodium iodide were added to the solution. The mixture was stirred at room temperature for 2 hours. To the thus obtained reaction mixture was added dichloromethane. The reaction mixture was then washed with water and N,N-dimethylformamide was removed. The solvent was removed by distillation from the resulting dichloromethane solution to give diphenylmethyl 7β-[2-phenylacetamido]-3-[(E)-3-(carbamoylmethylethylmethylammonio)-1-propenyl]-3-cephem-4-carboxylate iodide.

EXAMPLE 15

The reaction was carried out in a manner similar to Example 11 using the product obtained in Example 1. Thus p-methoxybenzyl 7β-[2-phenylacetamido]-3-[(E)-3-(carbamoylmethylethylmethylammonio)-1-propenyl]-3-cephem-4-carboxylate iodide N,N-dimethylformamide-solvated salt was obtained.

EXAMPLE 16

The reaction was carried out in a manner similar to Example 11 using the products obtained in Examples 4 to 8, respectively. Thus p-methoxybenzyl 7β-[2-phenylacetamido]-3-[(E)-3-(carbamoylmethylethylmethylammonio)-1-propenyl]-3-cephem-4-carboxylate iodide N,N-dimethylformamide-solvated salt was obtained.

COMPARATIVE EXAMPLE 1

After 20.0 g of p-methoxybenzyl 7β-[2-phenylacetamido]-3-[3-chloro-1-propenyl]-3-cephem-4-carboxylate (E/Z=25/75) was suspended in 250 ml of acetone, 29 g of sodium iodide was added to the suspension. The mixture was reacted at 25–30° C. for 3 hours, while stirring. After the reaction was completed, the solution was concentrated at a temperature below 25° C. under a reduced pressure of 100 mmHg and 60 ml of acetone was distilled off. The formed crystals were collected by filtration and washed successively with 50 g of 5% sodium thiosulfate aqueous solution, next with 50 g of ion exchange water and finally with 50 g of acetone to give 14.24 g of p-methoxybenzyl 7β-[2-phenylacetamido]-3-[3-iodo-1-propenyl]-3-cephem-4-carboxylate (content, 97.0%; E/Z=99/1). The yield of E-form was 59%.

COMPARATIVE EXAMPLE 2

After 2.0 g of p-methoxybenzyl 7β-[2-phenylacetamido]-3-[3-iodo-1-propenyl]-3-cephem-4-carboxylate (content: 97.0%) obtained in Comparative Example 1 was dissolved in a solvent mixture of 5 ml of dichloromethane and 2 ml of N,N-dimethylformamide, 0.44 g of 2-(ethylmethylamino) acetamide was added to the solution. The mixture was stirred at room temperature for 0.5 hour. The solvent was removed by distillation from the reaction mixture to give an oily substance containing 2.25 g of p-methoxybenzyl 7β-[2-phenylacetamido]-3-[(E)-3-(carbamoylmethylethylmethylammonio)-1-propenyl]-3-cephem-4-carboxylate iodide. Yield: 97%. The overall yield from the previous iodination step (Comparative Example 1) was 57%.

The 3-[(E)-1-propenyl]cephem compounds of the present invention are useful as the intermediates for producing cephem antibiotics. The 3-[(E)-1-propenyl]-cephem compounds can be produced in a good yield by isomerization of 3-[(Z)-1-propenyl]cephem compounds in the presence of an aromatic thiol. Among the cephem compounds, the 3-[(E)-3-chloro-1-propenyl]cephem compounds are reacted with tertiary amines to give 3-[(E)-3-ammonio-1-propenyl] cephem derivatives in a high yield.

What is claimed is:

1. A 3-{1-propenyl}cephem compound represented by formula (Ia):

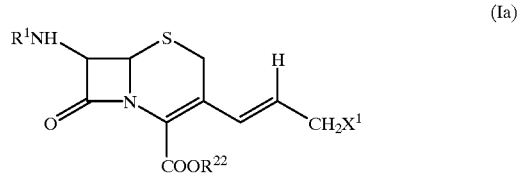

(Ia)

wherein $R^1$ is a hydrogen, a protective group for an amino group, or a group shown by formula (II):

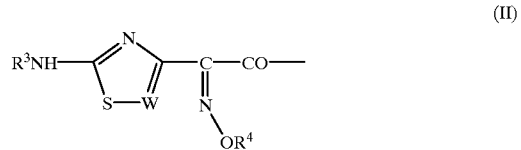

(II)

wherein $R^3$ is a protective group for an amino group, $R^4$ is a protective group for a hydroxyl group, and W is —CH= or —N=;

$R^{22}$ is a protective group for a carboxyl group, and $X^1$ is hydrogen or chlorine;

provided that $R^1$ is hydrogen when $X^1$ is hydrogen and when $X^1$ is hydrogen, $R^{22}$ is not diphenylmethyl;

wherein $R^1$ is a group represented by formula (II) in which the protective group for a hydroxyl group shown by $R^4$ is a lower alkyl group substituted by fluorine.

2. A 3-{1-propenyl}cephem compound represented by formula (Ia):

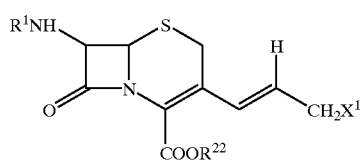
(Ia)
wherein $X^1$ is hydrogen or chlorine,
$R^1$ is phenylacetyl and
$R^{22}$ is selected from the group consisting of p-methoxybenzyl phenylmethyl,
provided that when $X^1$ is hydrogen, $R^{22}$ is not diphenylmethyl.
* * * * *